United States Patent [19]

Oku

[11] Patent Number: 5,280,781
[45] Date of Patent: Jan. 25, 1994

[54] GUIDE DEVICE FOR ENDOSCOPE

[75] Inventor: Toshio Oku, Tokyo, Japan

[73] Assignee: Kabushiki Kaisha Machida Seisakusho, Tokyo, Japan

[21] Appl. No.: 964,856

[22] Filed: Oct. 22, 1992

[30] Foreign Application Priority Data

Oct. 30, 1991 [JP] Japan .................. 3-311580

[51] Int. Cl.$^5$ ................................. A61B 1/00
[52] U.S. Cl. ............................ 128/4; 33/334
[58] Field of Search ............... 128/4, 6; 33/512, 333, 33/334, 354, 370, 371, 391, 398; 604/116; 606/1

[56] References Cited

U.S. PATENT DOCUMENTS

| | | | |
|---|---|---|---|
| 3,678,836 | 7/1972 | Dietz | 33/333 X |
| 4,164,817 | 8/1979 | Walker | 33/371 |
| 4,277,168 | 7/1981 | Oku | 128/4 X |
| 4,402,140 | 9/1983 | Nagae | 33/334 X |
| 4,630,649 | 12/1986 | Oku . | |
| 4,676,230 | 6/1987 | Miyazaki | 128/4 |
| 5,042,158 | 8/1991 | Schmelzer | 33/391 X |
| 5,224,467 | 7/1993 | Oku | 128/4 |

FOREIGN PATENT DOCUMENTS 62-63910 3/1987 Japan .
2-68024 3/1990 Japan .

Primary Examiner—Richard J. Apley
Assistant Examiner—Karen A. Jalbert
Attorney, Agent, or Firm—Fish & Richardson

[57] ABSTRACT

There is disclosed a guide device for guiding an endoscope. The guide device includes an elongate, tubular guide body so flexible as to be bent. An insertion portion of the endoscope is adapted to be inserted into and guided by the guide body. A direction indication mechanism is mounted on an inner periphery of a front end portion of the guide body. The direction indication mechanism includes an annular holder member, and a displacement member supported by the annular holder member for displacement circumferentially of the holder member under the influence of gravity. The endoscope itself is not provided with a direction indication mechanism, and by observing the displacement member from the inner side of the front end portion of the guide body, the direction is confirmed.

14 Claims, 5 Drawing Sheets

GUIDE DEVICE FOR ENDOSCOPE

BACKGROUND OF THE INVENTION

This invention relates generally to an elongate guide device for guiding an endoscope, and more particularly to a guide device having a direction indication mechanism by which the actual direction of each portion of an image obtained by the endoscope can be confirmed.

Generally, an endoscope comprises a body, an insertion portion extending from the body, and a rigid tip member mounted on a distal end of the insertion portion. An inspection window is provided at a distal end face of the tip member. An image entering from the inspection window is observed from an ocular portion of the body through an optical transmission system passing through the insertion portion.

When the insertion portion of the endoscope is inserted into a tube of a complicated shape so as to observe the inner surface of this tube, the actual direction of each portion of an image obtained or picked up by the endoscope is not confirmed, for example, because of a torsion of the insertion portion. Therefore, even if a defect can be found on the inner surface of the tube, the direction in which this defect exists (that is, whether the defect is in the right, the left, the upper or the lower direction) is not confirmed.

In order to overcome such a disadvantage, there have been proposed endoscopes, as disclosed in Japanese Laid-Open Patent Application Nos. 62-63910 and 2-68024, which incorporate a direction indication mechanism for confirming the actual direction of each portion of a picked-up image.

The direction indication mechanism of the former publication is provided within a tip member of the endoscope as shown in FIGS. 1 and 3 of this publication, and more specifically this mechanism is disposed between an inspection window and a distal end of an image guide, and has a ball 12 which is limited in axial movement by a pair of transparent plates 11 but is movable in circumferential and radial directions. Therefore, part of this ball can be observed as part of an image from an ocular portion provided on a body of the endoscope. The ball is always located at the lower side by gravity, and therefore the upper and lower directions with respect to the image can be confirmed by observing the ball. In embodiments shown in FIGS. 8 and 9 of this publication, there is used a transparent disk 15 rotatably supported by an annular bearing 14. The center of gravity of this disk 15 is eccentric from the axis of rotation thereof, and a direction indication mark 16 is provided on that portion of this disk always kept at the lower side. However, in the direction indication mechanism disclosed in this publication, the ball 12 or the mark 16 appears in the image, and accordingly the field of vision is narrowed, which has resulted in a problem that the image can not be observed satisfactorily.

The direction indication mechanism disclosed in the latter publication includes a forwardly-extending wire 26 secured to a tip member of the endoscope, and a weight 28 secured to a distal end of this wire. The wire is elastically deformed by the weight. The direction of deformation of the wire is the direction of the gravity, and by observing this, the upper and lower directions with respect to the image can be confirmed. In the direction indication mechanism of this publication, there has been encountered a problem that since the wire hanging down across the field of vision, the image can not be observed satisfactorily.

The basic construction of a guide device for an endoscope is disclosed in U.S. Pat. No. 4,630,649.

SUMMARY OF THE INVENTION

It is an object of this invention to provide a guide device for an endoscope in which the upper and lower directions with respect to an image obtained by the endoscope can be confirmed, and the field of vision is prevented from being narrowed, and the observation of the image is prevented from becoming unsatisfactory.

According to the present invention, there is provided a guide device for guiding an endoscope, the endoscope having an elongate insertion portion so flexible as to be bent, the guide device comprising:

(a) an elongate, tubular guide body so flexible as to be bent, the insertion portion of the endoscope being adapted to be inserted into and guided by the guide body; and (b) a direction indication mechanism mounted on an inner periphery of a front end portion of the guide body, the direction indication mechanism comprising annular holder means, and a displacement member supported by the annular holder means for displacement circumferentially of the holder means under the influence of gravity, and the displacement member being observable from the inner side of the front end portion of the guide body.

DESCRIPTION OF THE PREFERRED EMBODIMENTS

Figure 1:
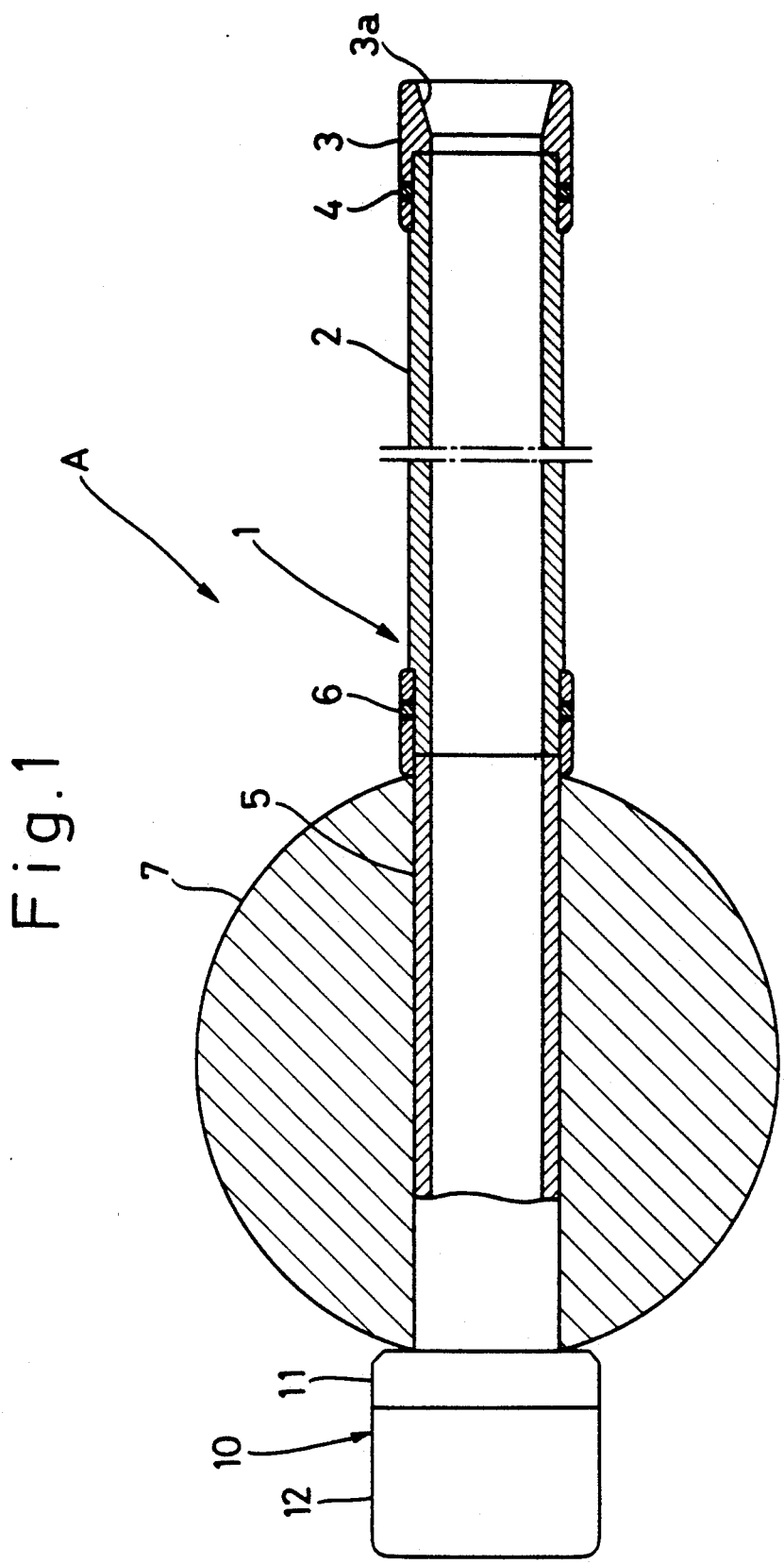
FIG. 1 is a cross-sectional view showing an overall construction of a guide device for an endoscope provided in accordance with the present invention.

The present invention will now be described with reference to the drawings. As shown in FIG. 1, a guide device A for an endoscope comprises a tube 2. The tube 2 is so flexible as to be bent, and has a relatively high strength to withstand tension and compression in an axial direction. The tube 2 comprises a metallic strip wound into a spiral shape, and adjacent turns of the spirally-wound strip are engaged with each other at their side portions. For example, the outer diameter of the tube 2 is 10 to 20 mm, and its length is several meters.

A rigid attachment 3 of a tubular shape is attached to a rear end of the tube 2, and is fixedly secured thereto by screws 4. A tapered opening 3a at the rear end portion of the attachment 3 serves as an inlet from which an insertion portion (later described) of an endoscope is inserted into the tube 2.

Figure 2:
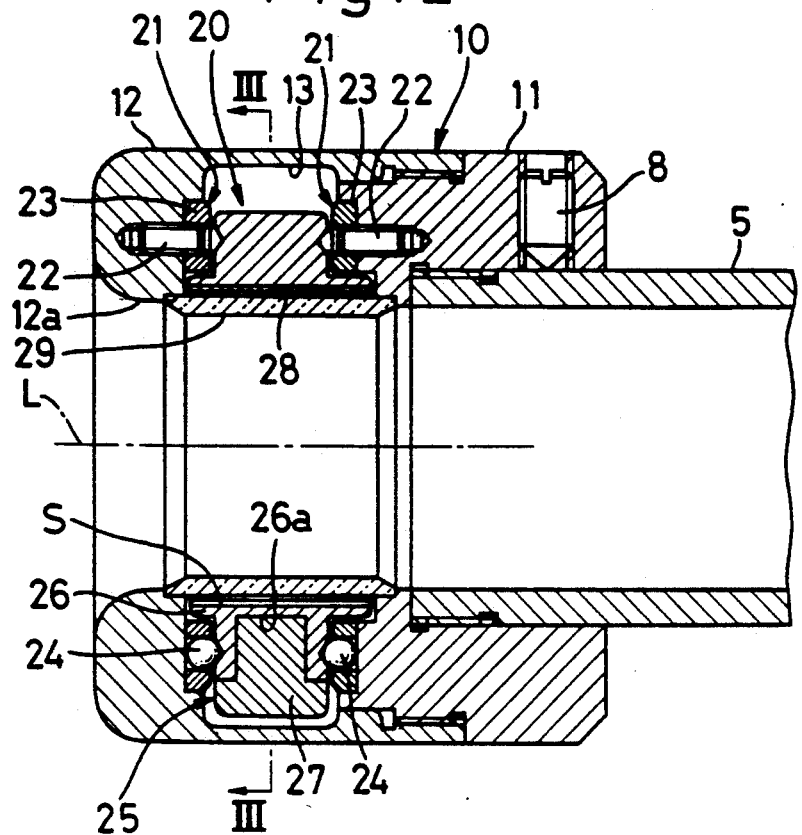
FIG. 2 is an enlarged cross-sectional view of a front end portion of the guide device.

A rigid connection tube 5 is attached to the front end of the tube 2, and is secured thereto by screws 6. A ball 7 is mounted on the outer periphery of the connection tube 5. A rigid attachment 10 of a tubular shape is attached to the front end portion of the connection tube 5. As shown in FIG. 2, the attachment 10 comprises a first half 11 and a second half 12. The first half 11 is threaded on the outer periphery of the front end portion of the connection tube 5, and fixedly secured thereto by a screw 8. The second half 12 is threaded on the outer periphery of the first half 11. An opening 12a at the front end portion of the second half 12 serves as an outlet from which the insertion portion of the endoscope is extended outwardly from the connection tube 5.

The tube 2, the attachment 3, the connection tube 5 and the attachment 10 jointly constitute a guide body 1.

Figure 3:
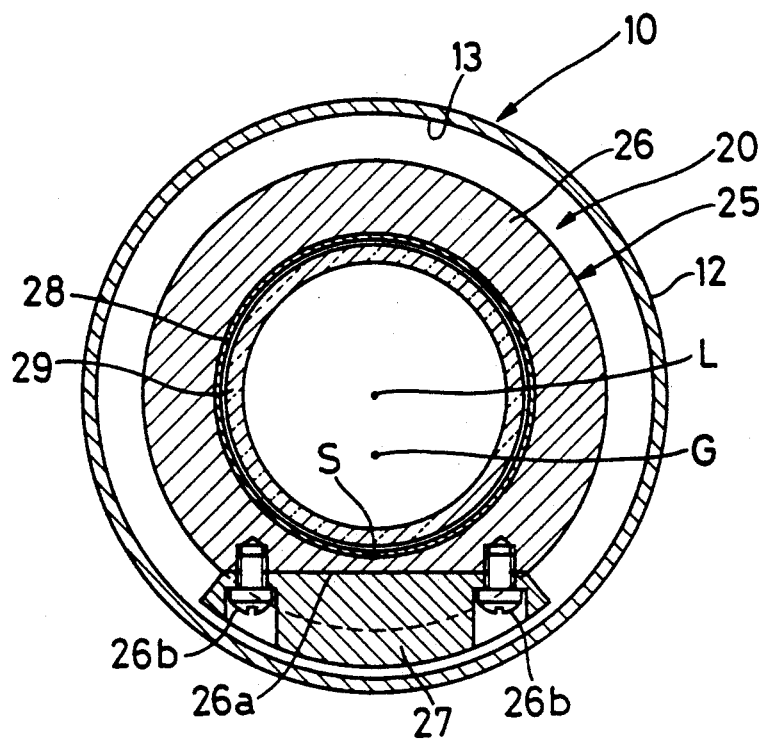
FIG. 3 is a cross-sectional view taken along the line III—III of FIG. 2.

As shown in FIGS. 2 and 3, an annular reception recess 13 is formed in the inner periphery of the attachment 10. A direction indication mechanism 20 of an annular shape is received in the reception recess 13. The direction indication mechanism 20 comprises a pair of annular bearings (holder means) 21 provided respectively on opposed side surfaces of the reception recess 13, and an annular displacement member 25 rotatably supported by the pair of bearings 21. Each bearing 21 includes an annular retainer 23 secured by screws 22 to the side surface of the reception recess 13, and a number of steel balls 24 supported by the retainer 23. The axis of rotation of the displacement member 25 is aligned with the axis L of the attachment 10 and the connection tube 5.

The displacement member 25 comprises a ring 26, a weight 27 made of a material greater in specific gravity than the material of the ring 26, and a direction indication sheet 28. The opposite sides of ring 26 are rotatably supported respectively by the pair of bearings 21, with its axis aligned with the axis L of the attachment 10. A recess 26a is formed in a predetermined portion of the outer peripheral surface of the ring 26, and the weight 27 is received in the recess 26a in such a manner that part of the weight 27 is projected outwardly from the outer peripheral surface of the ring 26, and the weight 27 is fixedly secured to the ring 26 by screws 26b. Therefore, the center G of gravity of the displacement member 25 is eccentric from the rotation axis L toward the weight 27, and the weight 27 is always located below the rotation axis L.

The direction indication sheet 28 is adhesively bonded to the inner peripheral surface of the ring 26. The direction indication sheet 28 is formed by bending a thin strip, shown in FIGS. 4 and 5, into an annular shape, and the entire length of this sheet 28 is slightly shorter than the length of the inner periphery of the ring 26. Therefore, when the direction indication sheet 28 is bonded to the inner peripheral surface of the ring 26, a gap S is formed between the opposed ends of the direction indication sheet 28. The gap S is disposed on a straight line passing through the axis L and the center G of gravity. Namely, the gap S is located in registry with the weight 27. Since the color of the inner peripheral surface of the ring 26 is different from the color of the inner peripheral surface of the direction indication sheet 28, the gap S can indicate a lower direction.

Figure 4:
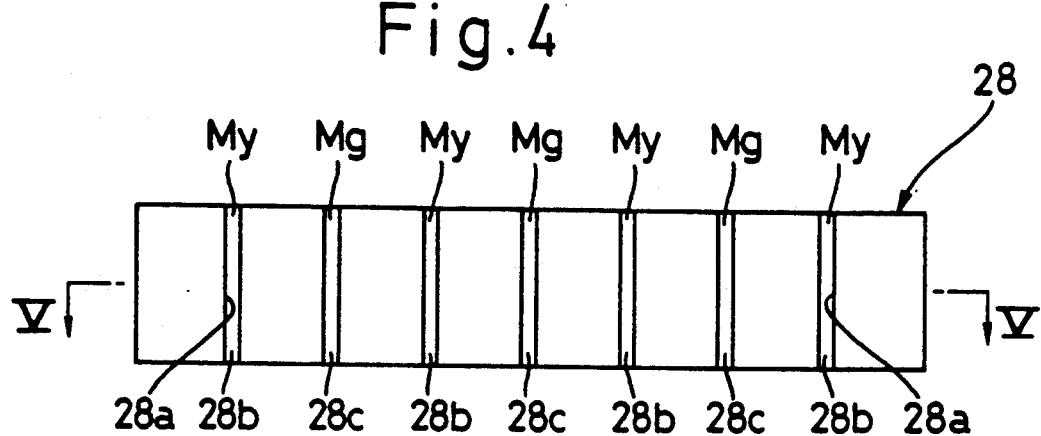
FIG. 4 is a developed view of a direction indication sheet.
Figure 5:
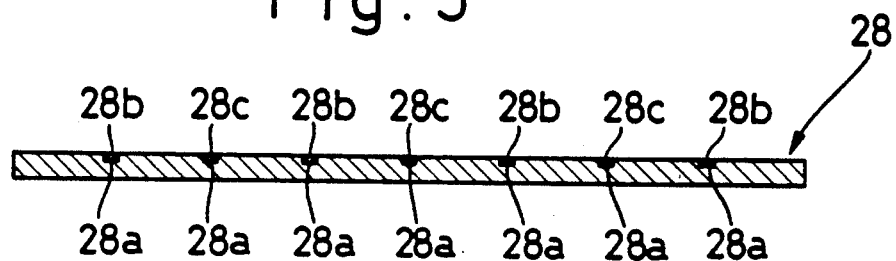
FIG. 5 is a cross-sectional view taken along the line V—V of FIG. 4, with the thickness shown in an exaggerated manner.

Seven grooves 28a are formed in the inner surface of the direction indication sheet 28, and are circumferentially spaced an angle of 45° from one another (Since the direction indication sheet 28 is thin, the grooves 28a are not shown in FIGS. 2 and 3 for illustration purposes, but are shown only in FIGS. 4 and 5). A yellow paint 28b and a green paint 28c (both of which are different in color from the inner peripheral surface of the direction indication sheet 28 and the inner peripheral surface of the ring 26) are alternately coated to the grooves 28a, so that three green marks Mg and four yellow marks My are provided. The green marks Mg indicate the upper direction, the right direction and the left direction, respectively. The yellow marks My indicate the obliquely upper right direction, the obliquely lower right direction, the obliquely upper left direction and the obliquely lower left direction. Paints of colors different from one another may be applied to all of the grooves 28, respectively.

A transparent tubular cover 29 is attached to the inner peripheral surface of the attachment 10 to close the reception recess 13. The cover 29 prevents foreign matters from intruding into the reception recess 13 to thereby ensure an angular movement of the displacement member 25. The cover 29 also enables the observation of the direction indication sheet 28 from the internal space of the attachment 10.

Figure 6:
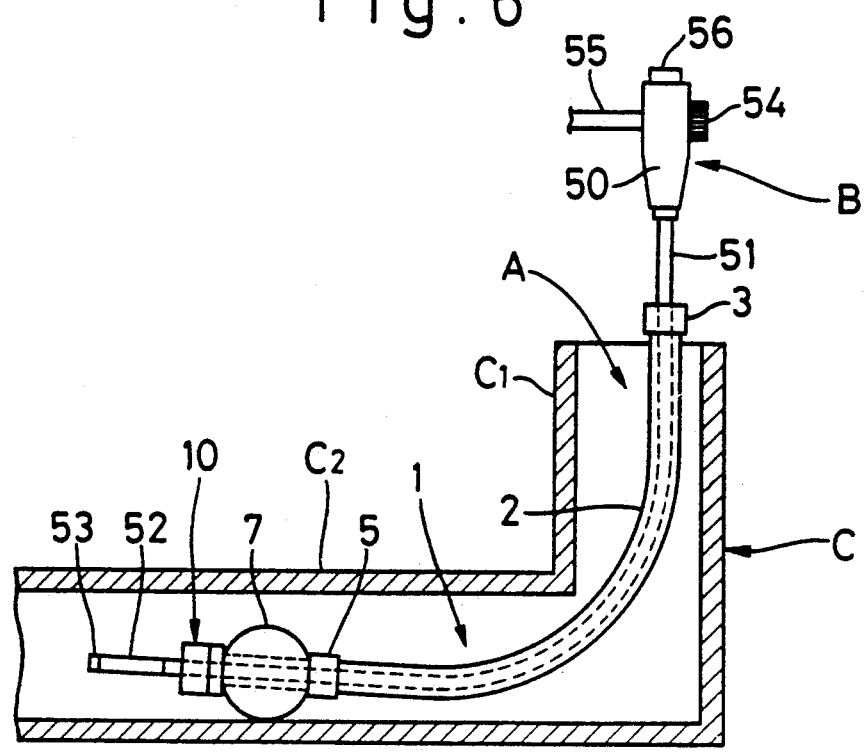
FIG. 6 is a cross-sectional view explanatory of the manner of guiding the endoscope by the guide device.

As shown in FIG. 6, the guide device A of the above construction is used for guiding the endoscope B into a tube C. The tube C has, for example, a vertical portion $C_1$ and a horizontal portion $C_2$ extending horizontally from a lower end of the vertical portion $C_1$. The endoscope B comprises a body 50, and the insertion portion 51 extending from the body 50. The front end portion of this insertion portion 51 serves as a bending portion 52, and a rigid tip member 53 is mounted on the front end of this bending portion 52. The insertion portion 51 and the bending portion 52 are both so flexible as to be bent. As is well known, the bending portion 52 is connected to a manipulation member 54, mounted on the body 50, via wires passing through the insertion portion 51 and the bending portion 52, and the bending portion 52 is bent by a remote manipulation of the manipulation member 54. An illumination window and an inspection window (both of which are not shown) are provided at the distal end face of the tip member 53. As is well known, the illumination window is connected to a light source (not shown) by an optical fiber passing through the insertion portion 51, the body 50 and a cable 55 extending from the body 50, and light from the light source is applied from the illumination window. As is well known, the inspection window is connected to an ocular portion 56, provided on the body 50, via an optical system including an optical fiber, and this arrangement enables the observation from the ocular portion 56. The endoscope may be of the type connectable to a television set.

For inspecting the inside of the tube C by the endoscope B, the endoscope B is inserted into the guide device A, and in this condition, the guide device A is inserted into the tube C until its lower end reaches the lower end of the vertical portion $C_1$ of the tube C. Then, the bending device 52 of the endoscope B is projected from the lower end of the guide device A, and in this condition the manipulation member 54 is manipulated to bend the bending portion 52 toward the horizontal portion $C_2$. In this condition, when the guide device A is pushed downwardly, the guide device A is guided by the bending portion 52 of the endoscope B to be fed toward the horizontal portion $C_2$. At this time, the ball 7, provided at the front end portion of the guide device A, moves in contact with the tube C, thereby smoothly feeding the guide device A. By this smooth feed of the guide device A, the tip member 53 of the endoscope B is concealed in the guide device A.

Then, the endoscope B is fed while it is guided by the guide device A, so that the bending portion 52 and the tip member 53 are projected from the front end of the guide device A. In this condition, the bending portion 52 is bent to observe the inner surface of the horizontal portion $C_2$ of the tube C to check whether or not there is any flaw on this inner surface. If a flaw is found, the endoscope B in once moved back without rotating it about its axis, until the tip member 53 is disposed slightly rearwardly of the direction indication sheet 28. In this condition, the gap S and the marks Mg and My of the direction indication sheet 28 are observed, and by doing so, the direction in which this flaw exists (that is, whether the flaw is in the right, the left, the upper or the lower direction) is confirmed.

As described above, the direction indication sheet 28 is provided in the guide device A, and when the inner surface of the tube C is being observed by the endoscope B, the direction indication sheet 28 is not in the field of vision of the ocular portion 56, and therefore the field of vision will not be narrowed by the direction indication sheet 28.

Figure 7:
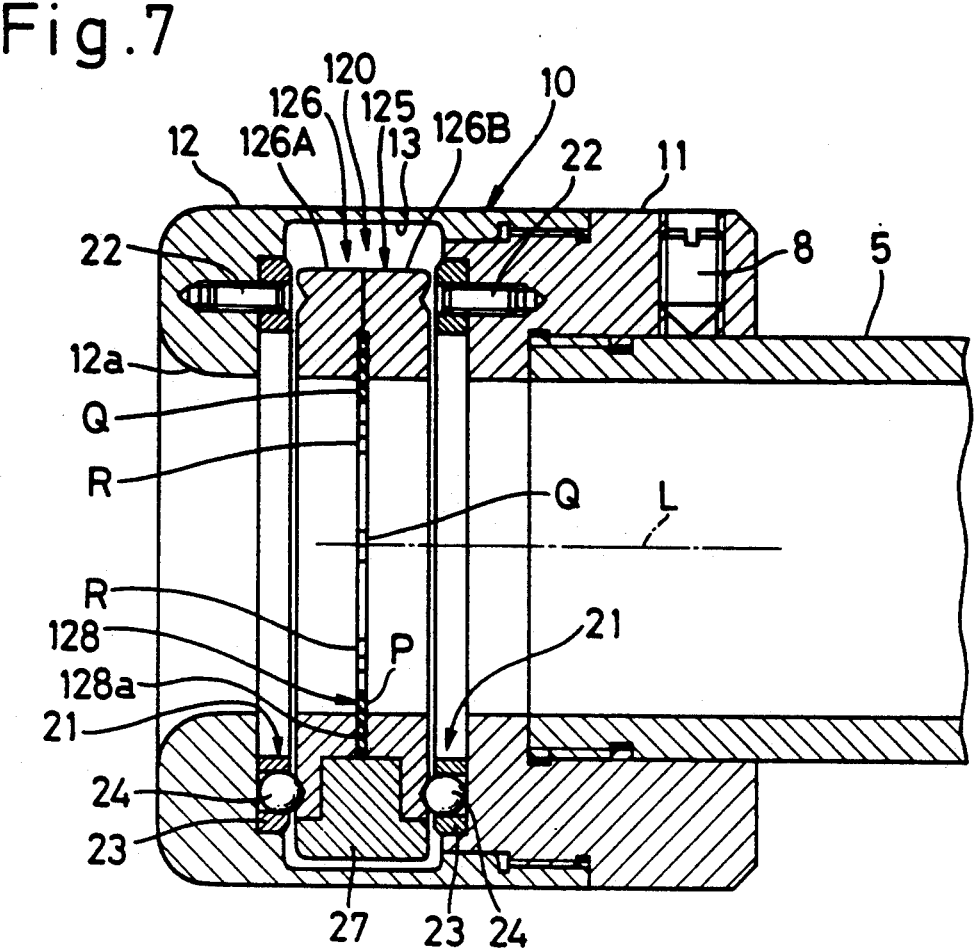
FIG. 7 is an enlarged cross-sectional view of a front end portion of a modified guide device.
Figure 8:
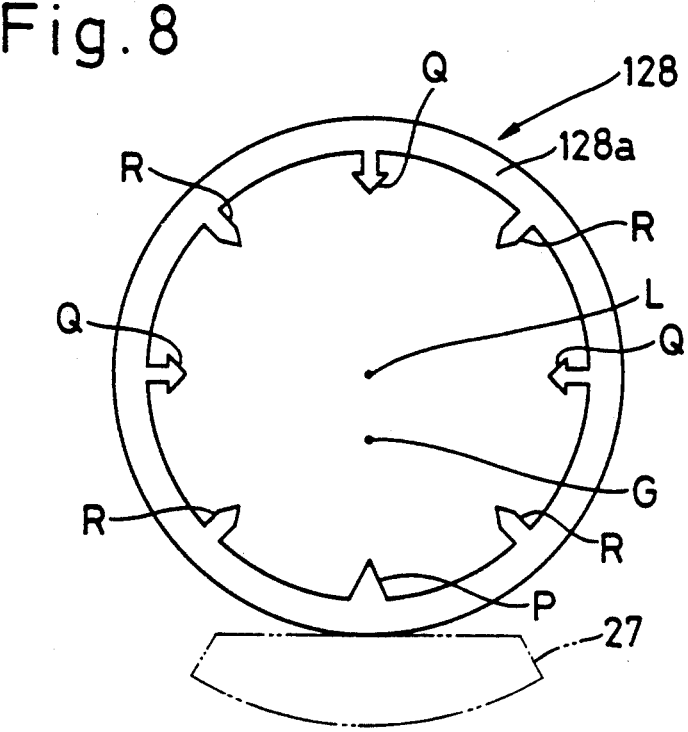
FIG. 8 is a front-elevational view of a direction indication sheet used in the guide device of FIG. 7.

Other embodiments of the invention will now be described. Those portions of the other embodiments corresponding to those of the preceding embodiment are designated by identical reference numerals, respectively, and detailed explanation thereof will be omitted. A guide device shown in FIGS. 7 and 8 is similar to the guide device of the preceding embodiment in that a direction indication mechanism 120 comprises a pair of bearings 21, and an annular displacement member 125 supported by these bearings 21; however, the former differs from the latter in that a ring 126 of the displacement member 125 comprises a pair of ring members 126A and 126B connected together by screws (not shown). A direction indication sheet 128 comprises an annular thin sheet, and is disposed in a plane perpendicular to an axis L. The direction indication sheet 128 includes a circular base 128a, and three kinds of projections P, Q and R which have different shapes from one another and extend radially inwardly from the inner periphery of the circular base 128a. The base 128a of the direction indication sheet 128 is sandwiched between and supported by the pair of ring members 126A and 126B, and the inner periphery of the base 128a coincides with the inner peripheral surfaces of the ring members 126A and 126B, so that only the projections P, Q and R are projected from these inner peripheral surfaces. The axis of rotation of the base 128a is aligned with the axis L of an attachment 10. One projection P of the direction indication sheet 128 is disposed in registry with a weight 27, and is always located at the lower side. The three projections Q are circumferentially spaced 90° and 180° from the projection P, that is, are disposed at the right, the left and the upper side, respectively. The four projections R are circumferentially spaced 45° from the projections P and Q, that is, are disposed at the obliquely upper right, the obliquely lower right, the obliquely upper left and the obliquely lower left, respectively.

In the case of using the guide device of FIGS. 7 and 8, when a flaw is found on the inner surface of the tube through the inspection window of the tip member of the endoscope projected from the front end of the guide device, the endoscope is moved back until the tip member is disposed rearwardly of the direction indication sheet 128, and by observing the projections P, Q and R, the direction of the flaw is confirmed. The direction indication sheet 128 is made of an elastomeric resin such as rubber, and therefore the projections P, Q and R will not affect the passage of the endoscope through the direction indication sheet 128.

Figure 9:
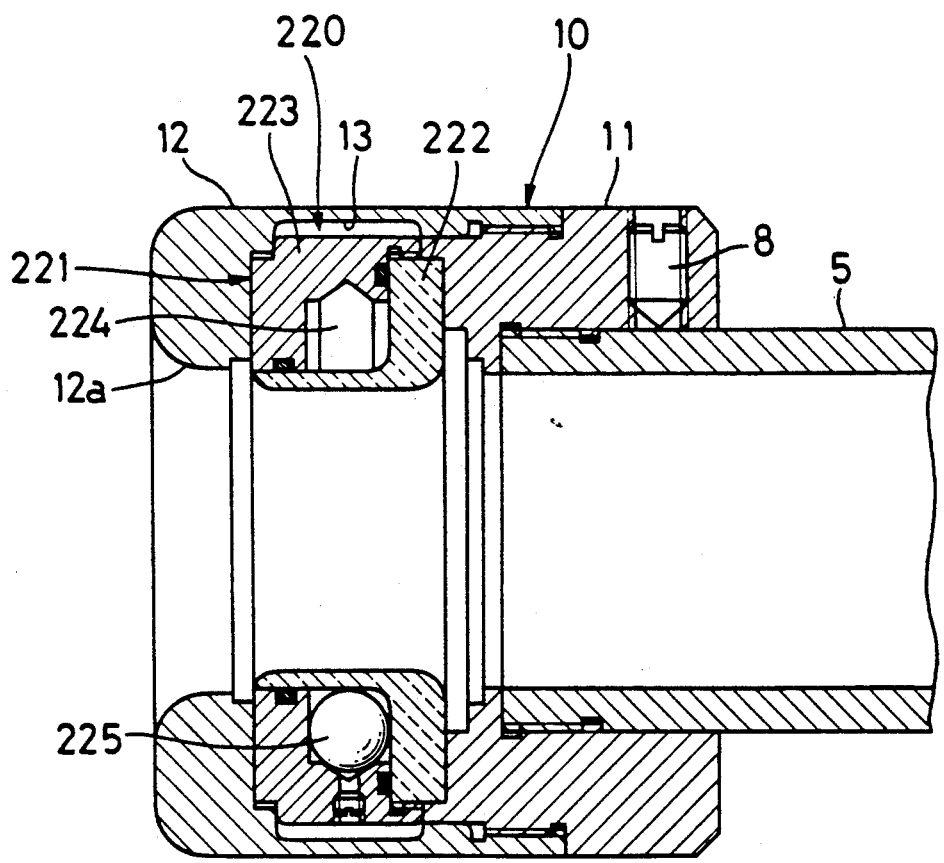
FIG. 9 is an enlarged cross-sectional view of a front end portion of another modified guide device.

A guide device shown in FIG. 9 is similar to the guide devices of the above two embodiments in that an annular direction indication mechanism 220 is received in a reception recess 13 in an attachment 10, but differs therefrom in the following points. The direction indication mechanism 220 comprises a holder means 221 composed of a pair of annular holder halves 222 and 223 of an L-shaped cross-section, and a steel ball (displacement member) 225 received circumferentially movably in an annular space 224 of a generally rectangular cross-section defined by the holder halves 222 and 223. The holder half 222 is made of a transparent material. The steel ball 225 is always located at the lower side. The steel ball 225 can be viewed through the inner peripheral portion of the transparent holder half 222 from the endoscope, and therefore the direction can be confirmed.

The present invention is not limited to the above embodiments, and various modifications can be made without departing from the scope of the invention. For example, the attachment 10 may be connected directly to the front end of the flexible tube 2 without using the connection tube 5 therebetween.

What is claimed is:

1. A guide device for guiding an endoscope, the endoscope having an elongate insertion portion so flexible as to be bent, said guide device comprising:
   (a) an elongate, tubular guide body so flexible as to be bent, the insertion portion of the endoscope being adapted to be inserted into and guided by said guide body; and
   (b) a direction indication mechanism mounted on an inner periphery of a front end portion of said guide body, said direction indication mechanism comprising annular holder means, and a displacement member rotatably supported by said annular holder means for displacement circumferentially of said holder means under the influence of gravity, and said displacement member being observable from the inner side of the front end portion of said guide body.

2. A guide device according to claim 1, in which said displacement member is annular, the center of gravity of said displacement member being eccentric from the axis of rotation thereof, and said displacement member having direction indication means indicating a specified direction.

3. A guide device according to claim 2, in which said displacement member comprises a ring, and a weight mounted on a predetermined portion of an outer periphery of said ring.

4. A guide device according to claim 2, in which said displacement member comprises a ring, and a direction indication sheet of a generally tubular shape attached to an inner peripheral surface of said ring, said direction indication sheet serving as said direction indication means.

5. A guide device according to claim 4, in which said direction indication sheet is thin, and has a length shorter than the length of the inner periphery of said ring, so that a gap is formed between the opposed ends of said direction indication sheet, said gap being located in the direction of eccentricity of said gravity center, and representing a lower direction.

6. A guide device according to claim 5, in which a paint mark representative of an upper direction is provided on an inner peripheral surface of said direction indication sheet and, is circumferentially spaced 180° from said gap, and two paint marks representative respectively of right and left directions are provided on the inner peripheral surface of said direction indication sheet in diametrically opposite relation to each other, and are circumferentially spaced 90° from said gap.

7. A guide device according to claim 2, in which said direction indication means comprises an annular direction indication sheet of an elastic material disposed in a plane perpendicular to an axis of said guide body, said direction indication sheet including an annular base, and a projection extending radially inwardly from said base, and said projection representing the specified direction.

8. A guide device according to claim 7, in which said displacement member comprises a pair of ring members connected together, said base of said direction indication sheet being held between said pair of ring members, and said projection projecting radially inwardly from inner peripheral surfaces of said pair of ring members.

9. A guide device according to claim 8, in which said projection is located in the direction of eccentricity of said gravity center, and represents a lower direction, and said direction indication sheet further has three projections which are circumferentially spaced 90° and 180° from said first-mentioned projection and project radially inwardly from said base, said three projections being different in shape from said first-mentioned projection.

10. A guide device according to claim 7, in which said direction indication sheet is made of rubber.

11. A guide device according to claim 1, in which said displacement member comprises a ball.

12. A guide device according to claim 11, in which said holder means having an annular space receiving said ball, said holder means having a transparent portion constituting an inner peripheral portion of said holder means.

13. A guide device according to claim 1, in which an annular reception recess is formed in the inner peripheral surface of the front end portion of said guide body, and said direction indication mechanism is received in said reception recess.

14. A guide device according to claim 13, in which said reception recess is closed by a transparent cover of a tubular shape, and said direction indication mechanism is isolated from the interior of said guide body by said cover.

* * * * *